United States Patent [19]
Hewson et al.

[11] Patent Number: 5,170,803
[45] Date of Patent: Dec. 15, 1992

[54] ESOPHAGEAL DISPLACEMENT ELECTRODE

[75] Inventors: Carl E. Hewson, Marshfield; John R. Hewson, Plymouth, both of Mass.

[73] Assignee: Brunswick Biomedical Technologies, Inc., Wareham, Mass.

[21] Appl. No.: 589,995

[22] Filed: Sep. 28, 1990

[51] Int. Cl.⁵ ............................................. A61N 1/05
[52] U.S. Cl. ..................................... 128/786; 128/642
[58] Field of Search ................ 128/639, 642, 780, 8, 128/786, 787, 419 D, 4, 696; 604/104–109

[56] References Cited

U.S. PATENT DOCUMENTS

| | | | |
|---|---|---|---|
| 3,060,972 | 10/1962 | Sheldon | 128/4 |
| 3,892,228 | 7/1975 | Mitsui | 128/4 |
| 4,245,624 | 1/1981 | Komiya | 128/4 |
| 4,686,996 | 8/1987 | Ulbrich | 128/642 |
| 4,706,688 | 11/1987 | Don Michael et al. | 128/642 |
| 4,718,407 | 1/1988 | Chikama | 128/4 |
| 4,919,112 | 4/1990 | Siegmund | 128/4 |
| 4,920,980 | 5/1990 | Jackowski | 128/642 |
| 4,960,134 | 10/1990 | Webster, Jr. | 128/786 |
| 5,056,532 | 10/1991 | Hull et al. | 128/419 D |

FOREIGN PATENT DOCUMENTS 1364350 1/1988 U.S.S.R. ................................. 128/8

Primary Examiner—Kyle L. Howell
Assistant Examiner—Kennedy J. Schaetzle
Attorney, Agent, or Firm—Wolf, Greenfield & Sacks

[57] ABSTRACT

An esophageal displacement electrode comprises a flexible tubular member designed to be inserted into the esophagus. An electrode is carried by the tube in the region of its distal end. The tube is hinged near the distal end which enables that end of the tube to displace laterally in the esophagus and laterally displace the esophagus. A displacement mechanism is disposed in the tube in the region of the hinge and is controlled from a point externally of the body for causing the distal end of the tube to displace laterally, and engage and displace the esophagus with it.

21 Claims, 4 Drawing Sheets

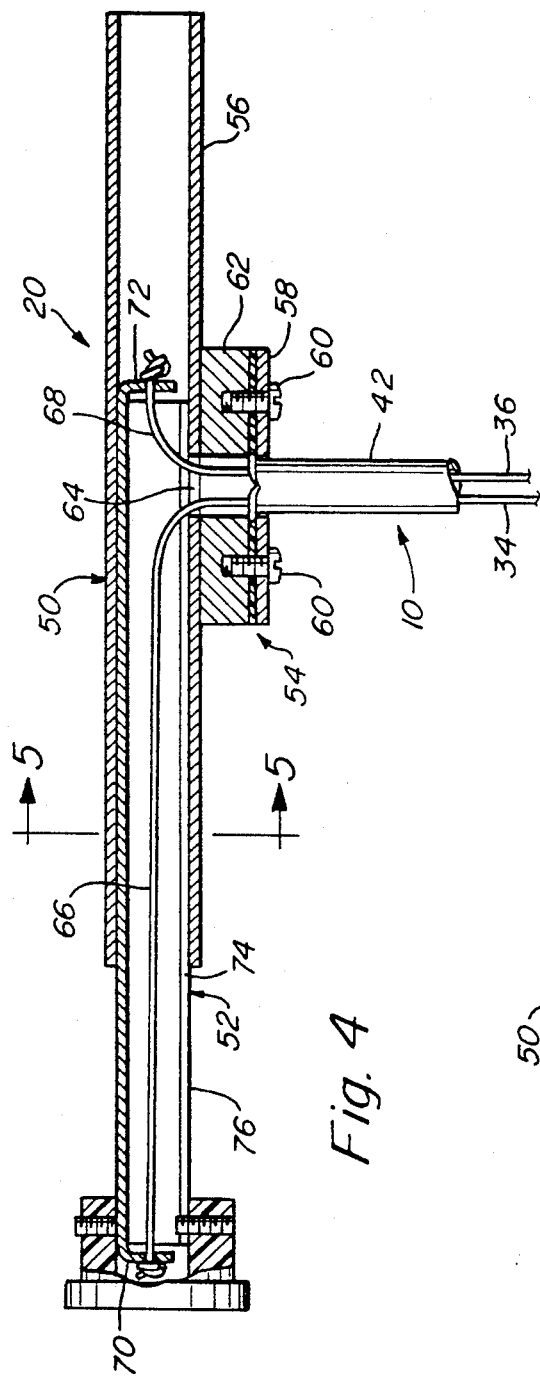
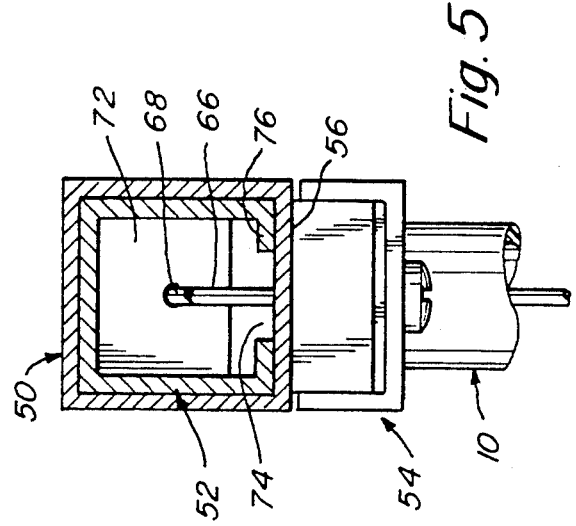

ESOPHAGEAL DISPLACEMENT ELECTRODE

FIELD OF THE INVENTION

This invention relates to esophageal electrodes and, more particularly, comprises such an electrode that can be moved laterally in and push the esophagus wall with it so that the electrode can be moved closer to an adjacent organ such as the heart.

There are a number of medical procedures in which esophageal electrodes are used for such purposes as defibrillating and pacing the heart as well as for stimulating breathing. Examples of the use of esophageal electrodes in such procedures are shown in several United States patents and pending applications including Nos. 4,574,807, 4,683,890, 4,735,206, and 4,960,133 and Ser. Nos. 421,807 filed Oct. 16, 1989 (now U.S. Pat. No. 5,036,848) 214,778 filed Jul. 5, 1988 (now U.S. Pat. No. 5,052,390); and 812,015 filed Dec. 23, 1985 (now abandoned). An esophageal electrode may also be used as an ECG pickup. Those patents and applications are herein incorporated by reference. Many of these procedures may be substantially enhanced and facilitated if the electrode is capable of being moved close to the organ of the body being treated such as the ventricles of the heart.

Frequently patient care in a hospital and emergency care outside a hospital require ventricular pacing. Customarily, this is an invasive procedure and must therefore be performed in a sterile atmosphere, and the procedure requires a considerable period of time to perform. Many of the patents and applications identified above disclose a method and apparatus employing an internal, noninvasive esophageal electrode in combination with an external chest electrode, which are much more convenient to use, more efficient in performing the intended function, and do not require the presence of a physician.

The techniques described in the above-identified patents and applications relating to pacing and/or defibrillation may be made more efficient if the esophageal electrode is positioned as close to the ventricle of the heart as possible. The closer the electrode is to the ventricle, the less electrical energy is needed to perform the pacing or defibrillating functions, and the more confident the attendant may be that the current flow between the internal and external electrodes is along the desired path.

The present invention is directed to an esophageal displacement electrode to achieve greater efficiency in the practice of such procedures. In the past, attempts to position an electrode closer to the heart by way of the esophagus have employed an inflation cuff having an electrode disposed on its surface. Inflation of the cuff stretched the esophagus so as to place the electrode nearer to the heart. This technique is limited, however, because of the limits upon the stretchability of the esophagus. The acceptable limit of stretching the esophagus diameter is considered to be approximately 1½ inches. In accordance with the present invention, the esophagus is not stretched, but rather it is displaced laterally toward the heart. In accordance with the present invention, a thin, semi rigid plastic tube which carries an electrode at its distal end has a mechanism incorporated into it which enables the user to cause the distal end of the tube to bend and press against the wall of the esophagus. The mechanism is of sufficient strength to cause the esophagus to displace under the pushing force of the electrode. To enable the tube to bend readily under the action of the mechanism, the tube is crimped so as to define a hinge at the distal region of the tube.

The mechanism for deflecting the distal end of the tube includes a rigid pin having a cord connected at each end and which is aligned generally parallel to the axis of the tube and positioned at the distal portion thereof in the vicinity of the hinge. One cord attached to the proximal end of the pin extends out the proximal end of the tube, while the other cord attached to the distal end of the pin extends through a port located distally of the hinge in the tube and reenters the tube through a second port proximal of the hinge and then extends out the proximal end of the tube. By pulling on the cord attached to the distal end of the pin, the pin may be positioned adjacent the distal port and continued pulling of the cord will cause the tube to bend at the hinge.

The two cords attached to the ends of the pin are manipulated by a control mechanism including a sleeve and slide attached to the proximal end of the tube. When the slide is moved in one direction, the pin is pulled proximally in the tube to a position adjacent the hinge so as not to cause any bending of it. If the pin is positioned to span the hinge, it provides rigidity to the tube and will assist in inserting the tube in the esophagus. When the slide is moved in the opposite direction, the pin is moved distally in the tube beyond the hinge to the distal port, and continued motion of the slide in that direction will cause the distal end of the tube to bend and move the electrode firmly against the esophageal wall.

The tube may be inserted either orally or nasally into the esophagus, and when the electrode is disposed in the esophagus adjacent the heart, the control mechanism may be operated in one direction to displace the electrode and esophagus toward the heart. After the procedure is completed, the tube carrying the electrode may be straightened by moving the control mechanism in the opposite direction, and thereafter the tube may be removed from the esophagus.

This invention will be better understood and appreciated from the following detailed description of a preferred embodiment thereof, selected for purposes of illustration and shown in the accompanying drawings.

BRIEF DESCRIPTION THE FIGURES

FIG. 4 is a side view of the control mechanism for the electrode shown in FIGS. 1-3 and suggesting in full and broken lines the alternate positions for the control slide; and FIG. 5 is a cross-sectional view of the control mechanism taken along section line 5—5 in FIG. 4.

DETAILED DESCRIPTION OF THE INVENTION

Figure 1:
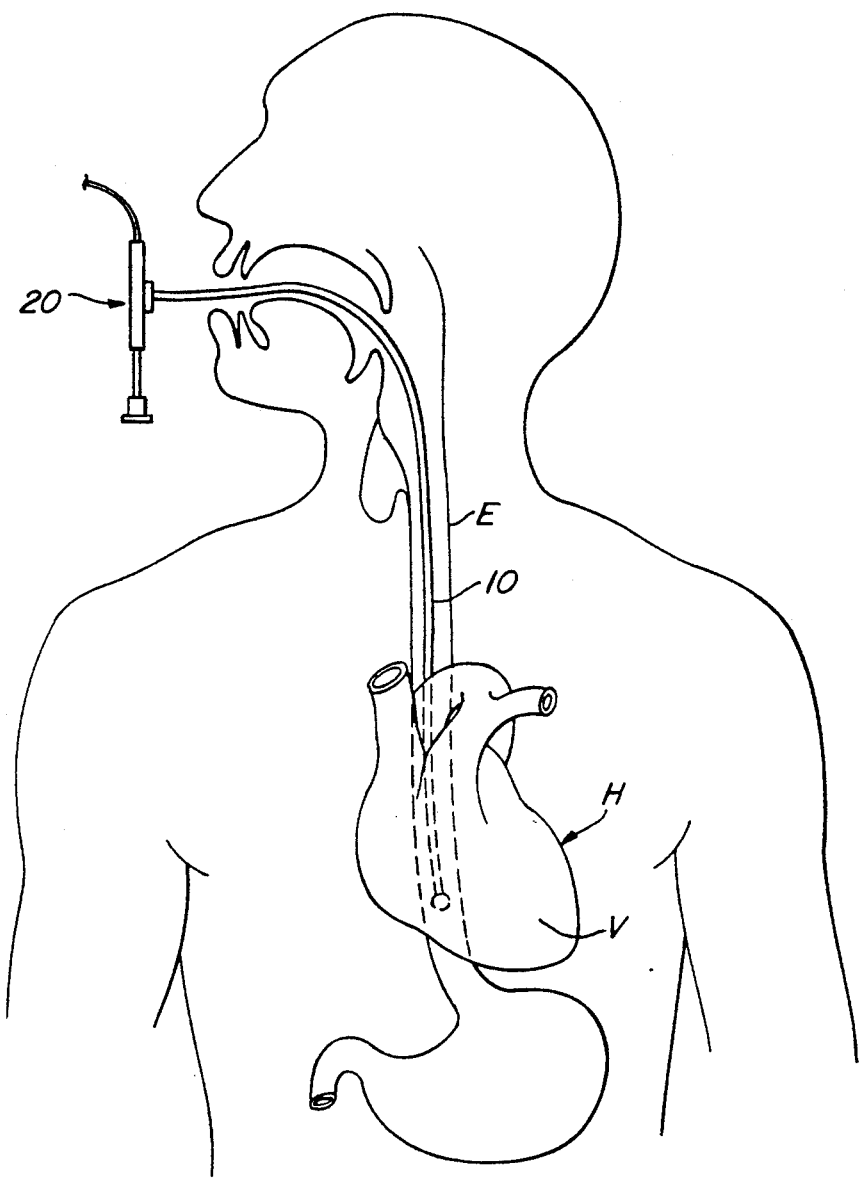
FIG. 1 is a diagrammatic front view of a patient suggesting the heart and esophagus and showing without details the esophageal displacement electrode of the present invention disposed in the esophagus.

In FIG. 1 the torso and head of a patient are shown along with the patient s heart H and esophagus E. The esophagus is located posterior and spaced from the ventricle V. The esophageal displacement electrode shown extends through the patient's mouth to the lower third of the esophagus with its distal end located close to the ventricle V. The present invention enables the distal end of the esophageal displacement electrode to displace within the esophagus and push the esophageal wall closer than normal to the heart and thereby place the esophageal displacement electrode in closer proximity to it. This is illustrated in FIGS. 2 and 3.

The esophageal displacement electrode includes a semi rigid plastic tube 10 made of nylon or other suitable material which may be approximately 20 inches long and approximately 3/16-inch in diameter. The tube should be semi rigid, much like a gastric tube, and be relatively torque free. The distal end 12 of the tube carries an electrode 14, preferably spherical in shape and having a stem 16 that fits within the distal end of the tube. The electrode may be pressed in place or suitably fastened by other means. In the preferred form, the electrode 14 is ¼ inch in diameter, which just exceeds the diameter of the tube 10 so that the ball will make positive contact with the esophageal wall when the distal end 12 of the tube 10 is displaced.

The tube 10 is carried by a control mechanism 20 shown in FIG. 4 which is connected to a displacement mechanism 22 disposed in the tube. The control mechanism is located at the proximal end of the tube outside the mouth when the esophageal displacement electrode is placed in the esophagus as shown in FIG. 1.

Figure 2:
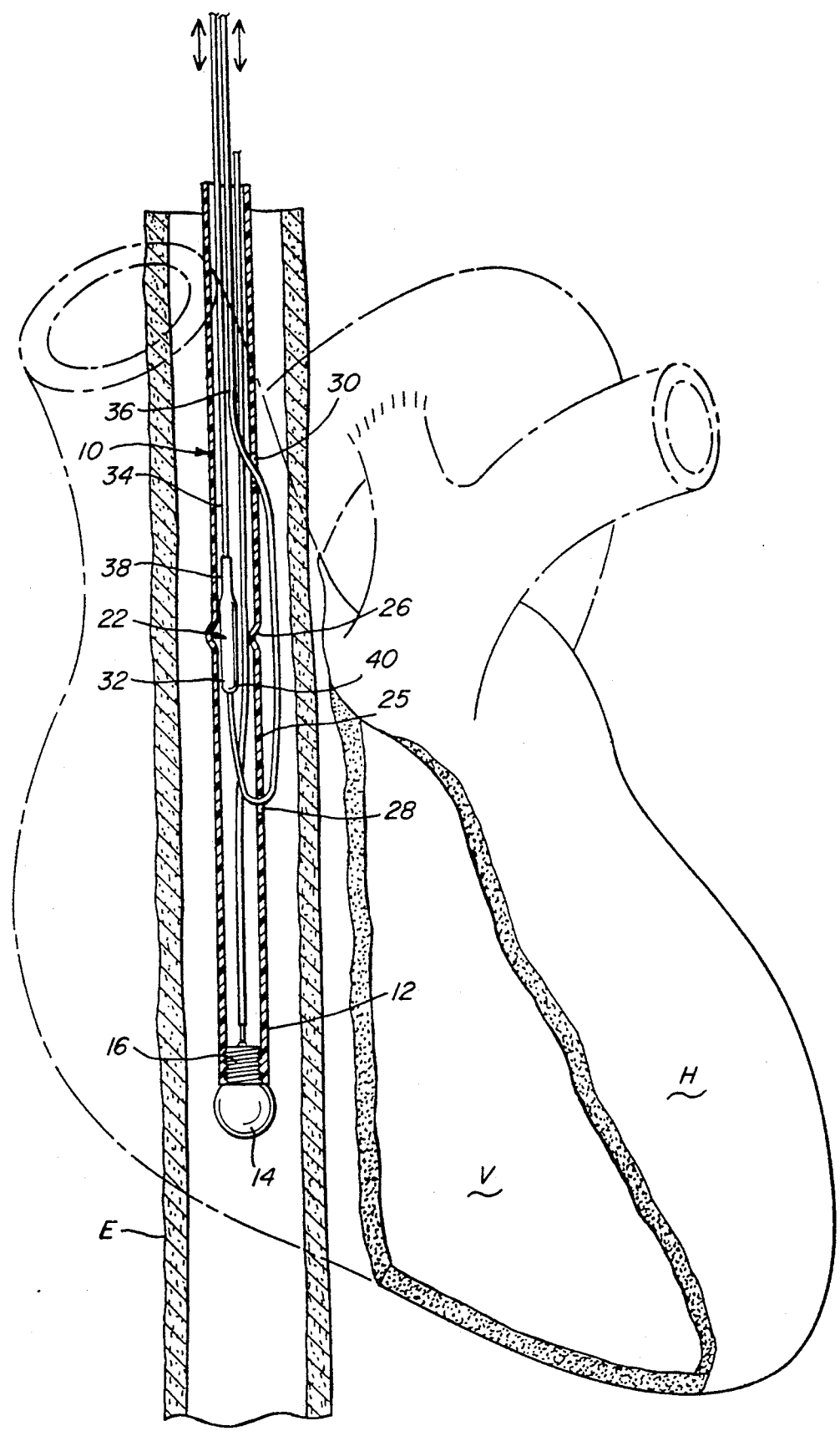
FIG. 2 is an enlarged cross-sectional view of esophageal displacement electrode in the esophagus and with the distal end thereof in the undisplacement position.
Figure 3:
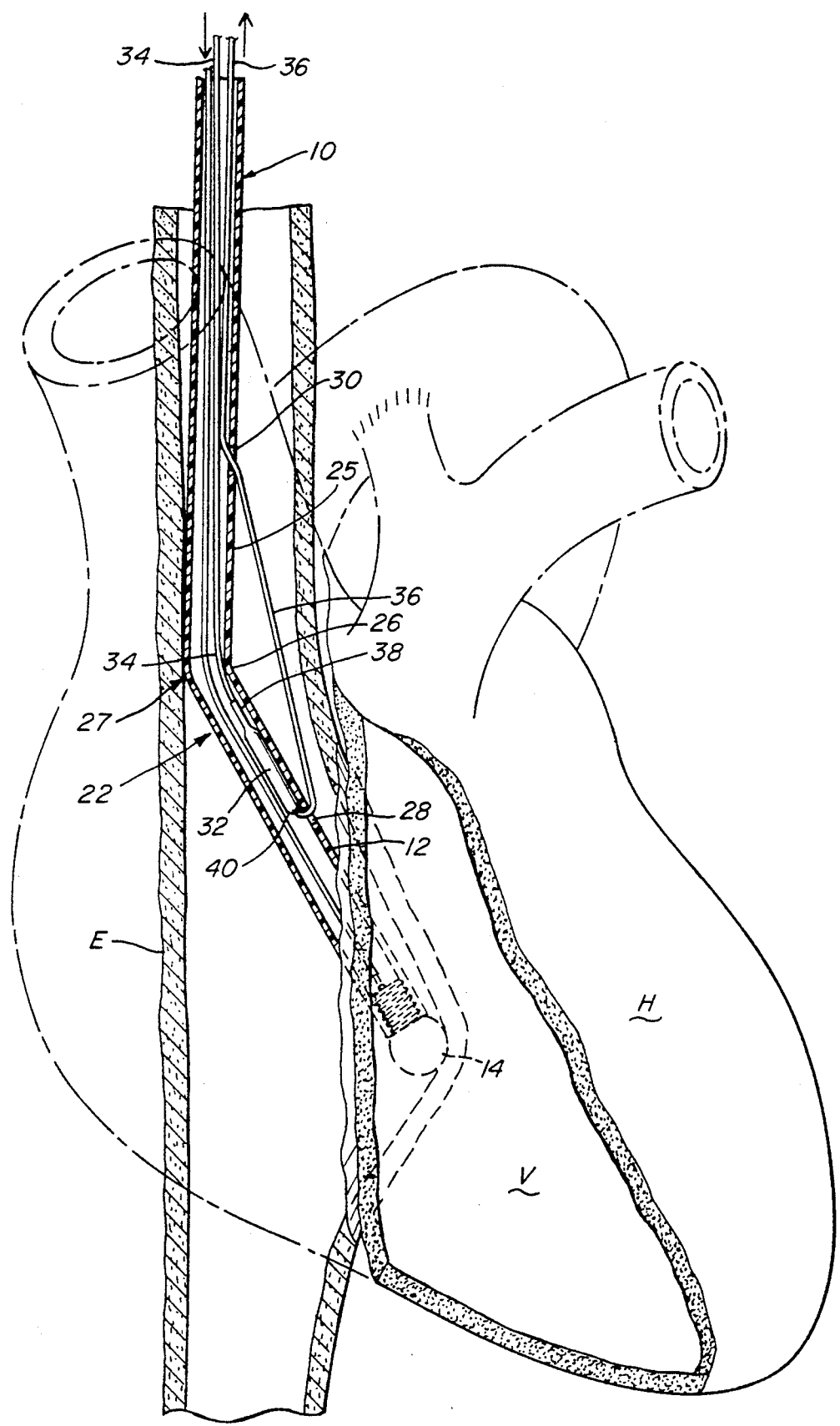
FIG. 3 is a view similar to FIG. 2 but showing the electrode in its displaced position.

The tube 10 is crimped as suggested at 26 in FIGS. 2 and 3 so as to form a hinge 27 in the tube, which enables it to bend readily at that point. In the wall 25 of the tube 10, ports 28 and 30 are formed on opposite sides of the hinge 27, each spaced approximately an inch therefrom. While in the embodiment shown, each of the two ports is approximately one inch from the crimp 26, that dimension as well as others given may be varied to suit the particular application, as is more fully described below.

A rigid pin 32 is disposed in the tube 10 and extends generally parallel to the tube axis. The pin may be made of metal, rigid plastic, or any other material having sufficient rigidity to prevent the tube 10 from bending at the crimped area 26 when the pin spans the hinge.

A pair of cords 34 and 36 are connected to the proximal and distal ends 38 and 40, respectively, of pin 32 and extend proximally in the tube 10 out its proximal end 42 and into the control mechanism 20. Cord 34 extends directly from the proximal end of the pin 32 within the tube 10 to the control mechanism 20, while cord 36 extends from the distal end 40 of the pin, out the tube 10 through port 28 and from that point it extends proximally externally of the tube, spanning the crimped portion 26 to the port 30 where the cord reenters the tube 10 and extends in the tube to the control mechanism 20. As is evident from FIGS. 2 and 3, the location of the pin 32 may readily be changed by pulling one or the other of the cords 34 or 36 in a proximal direction.

Pin 32 is somewhat shorter than the distance between the crimped portion 26 of the tube and the lower port 28. Travel of the pin 32 in the tube 10 in a distal direction is limited by the location of port 28. The size of pin 32 is such that it cannot be drawn through port 28 and therefore when the pin 32 reaches its lowermost point and a continued pull is exerted on cord 36, the distal portion of the tube 10 is caused to deflect from the position shown in FIG. 2 to that shown in FIG. 3. While the tube 10 is displaced or bent about the hinge 27 by pulling on cord 36 when pin 32 has reached its lowermost position, merely by releasing tension on the cord 36, the natural bias of the tube 10 to the configuration of FIGS. 1 and 2 will cause it to return to the shape shown therein.

The control mechanism 20 shown in FIG. 4 is connected to the distal ends of the cords 34 and 36 to operate the displacement mechanism 22 by taking up one cord and playing out the other. The control mechanism 20 includes a sleeve 50, rectangular in cross-section in the embodiment shown, and containing a slide 52. A bracket 54 is secured to the bottom wall 56 of sleeve 50 and retains the proximal end 42 of tube 10 in place. The bracket 54 includes a bar 62 and clamping plate 58 that sandwich the tube end, and the plate 58 is secured to the bar 62 by screws 60.

The cords 34 and 36 enter the sleeve 50 through a port 64 in bottom wall 56, aligned with the proximal end 42 of the tube 10 when the tube is secured to the bracket 54. The proximal ends 66 and 68 of the cords are respectively connected to flanges 70 and 72 carried by the slide 52. In FIG. 4, slide 52 is shown in the position that places the pin 32 in the tube in the position shown in FIG. 2. When the slide is moved to the right as viewed in FIG. 4, the pin 32 moves to its lowermost position in tube 10 and the tube is deflected, as shown in FIG. 3. Because the slide 52 is generally U-shaped with an opening 74 in its bottom wall 76 that rests upon the bottom wall 56 of sleeve 50, movement of the slide 52 in the sleeve 50 does not in any way interfere with the movement of the cords 34 and 36 in response to displacement of the slide.

The esophageal displacement electrode typically may be used in the following manner. Assume that the esophageal displacement electrode is part of a pacing mechanism as shown in U.S. Pat. No. 4,735,206, supra. The tube 10 is inserted into the esophagus either through the mouth or the nasal passage to a depth wherein the electrode 14 is adjacent the ventricle V of the heart. The external electrode also forming part of the pacer is mounted on the chest of the patient and the controls, etc. are properly set. In order to reduce the amount of electrical energy required to effect pacing, the operator moves the slide 52 to the right as shown in FIG. 4 which will cause the pin 32 to move downwardly in the tube 10 so that its distal end 40 is immediately adjacent the port 28. Further movement of the slide 52 in that direction will cause the distal portion of the tube 10 to deflect and push the esophagus toward the ventricle V and place the electrode 14 closer to it, as shown in FIG. 3. With the electrode in the displaced position of FIG. 3, the pacing pulses are imposed across the electrodes. When the procedure is completed, the operator may move the slide 52 back to the position of FIG. 4, which will relieve the tension on the cord 36 and allow the tube 10 to return to the position of FIG. 2. Thereafter the tube 10 may be withdrawn.

From the foregoing description, those skilled in the art will appreciate that the present invention provides a very convenient means of enabling an operator to place the esophageal displacement electrode very close to the heart or other organ by means of a noninvasive procedure and thereby reduce the energy required to carry out the particular procedure such as pacing or defibrillation upon the patient. It will also be appreciated that while a specific embodiment is shown in the drawings, modifications may be made thereof without departing from this invention. For example, while a pin is shown as applying the bending force to the interior of the tube, other configurations for the device may be employed. Any structure which will not pass through the lower port 28 and will not interfere with the action of the hinge 27 will cause the tube 10 to deflect when the cord attached to it and exiting the tube through the port 28 is tensioned It should, if necessary, also stiffen the hinge portion of the tube when it is being inserted in the esophagus. The member which applies the bending force must be capable of moving freely in the tube under the operation of the control 20 so as to be readily movable in response to actuation of the control. The tube 10 could, of course, carry more than one electrode. For example, in the earlier patents, supra, a number of spaced contact rings are shown carried by the tube.

Because modifications may be made of the invention without departing from its spirit, it is not intended that the scope of the invention be limited to the specific embodiment illustrated and described. Rather, the scope of this invention is to be determined by the appended claims and their equivalents.

What is claimed is:

1. An esophageal displacement electrode comprising:
   a flexible hollow tube having proximal and distal ends for insertion of the distal end into the esophagus to the region of the ventricles of the heart and the proximal end disposed externally of the body;
   an electrode carried by the tube at its distal end;
   a bendable section provided in the tube a short distance proximally of the distal end having means enabling the tube distally of the section to deflect laterally and displace the adjacent portion of the esophagus toward the ventricles and place the electrode close to the ventricle; and
   displacement means disposed in the tube and controlled from a point externally of the body for causing the distal end of the tube to deflect and displace the esophagus.

2. An esophageal displacement electrode as described in claim 1 wherein the displacement means includes means for resisting bending of the tube at the bendable section until the displacement means causes the distal end of the tube to deflect.

3. An esophageal displacement electrode as described in claim 1 wherein the displacement means includes a member disposed in the tube in the vicinity of the bendable section,
   and means for moving said member, enabling movement of said member to a position distal to the bendable section, said means for moving including means attached to the member and operable from a location externally of the body for causing it to push against and deflect the portion of the tube distal to the bendable section so as to place the electrode closer to the heart.

4. An esophageal displacement electrode as described in claim 3 wherein the means attached to the member includes a cord connected to the member, a distal and a proximal port in the tube disposed on opposite sides of the bendable section, said cord exiting the tube through the distal port and reentering the tube through the proximal port and extending through the tube to the control mechanism.

5. An esophageal displacement electrode as described in claim 4 wherein means prevent the member from being drawn out the tube through the distal port.

6. An esophageal displacement electrode as described in claim 5 further including a control mechanism for controlling said displacement means, said control mechanism includes a sleeve and slide disposed in the sleeve and attached to the cord for pulling the cord so as to move the member to the extreme distal position and displace the portion of the tube distally of the bendable section.

7. An esophageal displacement electrode as described in claim 6 wherein a second cord is attached to the member and extends from the member proximally out of the tube to the control mechanism.

8. An esophageal displacement electrode as described in claim 7 wherein the control mechanism includes means attached to the cords for taking up one of the cords while playing out the other.

9. An esophageal displacement electrode as described in claim 8 wherein the control mechanism includes a sleeve and a slide movable in the sleeve for taking up and playing out the cords.

10. An esophageal displacement electrode comprising:
    a flexible hollow tube having proximal and distal ends for insertion of the distal end into the esophagus to the region of the ventricles of the heart and the proximal end disposed externally of the body;
    an electrode carried by the tube at its distal end;
    means in the tube enabling the distal end thereof to displace laterally with respect to the tube axial so as to engage and press against the esophagus to displace the esophagus wall toward the heart;
    and displacement means disposed in the tube and controlled from a point externally of the body for causing the distal end of the tube to displace the esophagus and place the electrode nearer the heart.

11. An esophageal displacement electrode as described in claim 10 wherein the displacement means includes a member, a cord connected to the member and extending out the proximal end of the tube and means attached to said cord for moving said cord, thereby enabling movement of said member in the tube to a point below the first-named means.

12. An esophageal displacement electrode as described in claim 11 wherein the member is a rigid pin extending longitudinally of the tube,
    and said cord spans the first-named means externally of the tube.

13. An esophageal displacement electrode as described in claim 12 wherein a pair of ports are provided in the tube, one on each side of the first-named means,
    and said cord exits from the tube in the port distally of the first-named means and reenters the tube through the other port and extends proximally therefrom in the tube to the proximal end of the tube.

14. An esophageal displacement electrode as described in claim 10 wherein the first-named means is a crimp in the tube causing it to bend at the crimp when the distal end of the tube is pulled proximally by the displacement member.

15. An esophageal displacement electrode comprising:
    a flexible hollow tube having proximal and distal ends for insertion of the distal end into the esophagus;

an electrode carried by the tube in the region of its distal end;

said tube having hinge means enabling the distal end of the tube to displace laterally in the esophagus and laterally displace the esophagus;

and displacement means disposed in the tube and controlled from a point externally of the body for causing the distal end of the tube to displace laterally, and engage and displace the esophagus.

16. A method of noninvasively placing an electrode in the body closely adjacent a selected body organ comprising the steps of:

inserting into the esophagus an elongated member carrying an electrode at its distal region;

and displacing the distal region of the elongated member laterally, through the bending of said elongated member, in the esophagus to place the distal region against only one side of the esophageal wall and displace the esophagus toward the selected organ.

17. A method as described in claim 16 including the additional step of controlling the displacing of the distal region from a location externally of the body.

18. A method as described in claim 17 wherein the elongated member further includes a longitudinally extending cord operatively connected to the distal region, and further, the step of controlling the displacing the distal region of the elongated member includes the step of controlling longitudinal movement, from a position outside the body, of the cord.

19. A method as described in claim 18 wherein the elongated member further includes a mass member attached to the distal end of said cord and an aperture defined in the elongated member, with walls on either side thereof, through which the cord is fed and through which the mass member cannot pass, and further, the step of controlling the displacing the distal region of the elongated member further includes the step of causing the mass member to abut against the walls on either side of the aperture in said elongated member.

20. An esophageal displacement electrode comprising:

a flexible tubular member having proximal and distal ends for insertion of the distal end into the esophagus;

an electrode disposed within the tube at its distal end;

said tube having hinge means enabling the distal end of the tube to displace laterally;

force means, for causing the distal end of the tube to laterally displace the esophagus and place the electrode in a desired location close to a heart ventricle;

and means, external to the body, for controlling said force means.

21. An esophageal displacement electrode as claimed in claim 20 further including a member within said tube, and wherein said displacement means includes a cord attached to said member, a portion of which is external to said tube, said cord for moving said member and displacing said tube.

* * * * *